US006200765B1

United States Patent
Murphy et al.

(10) Patent No.: US 6,200,765 B1
(45) Date of Patent: Mar. 13, 2001

(54) NON-INVASIVE METHODS TO DETECT PROSTATE CANCER

(75) Inventors: Gerald P. Murphy, Seattle; Alton L. Boynton, Redmond; Eric H. Holmes, Bothell; Robert J. Barren, III, Seattle, all of WA (US)

(73) Assignee: Pacific Northwest Cancer Foundation, Seattle, WA (US)

(*) Notice: Subject to any disclaimer, the term of this patent is extended or adjusted under 35 U.S.C. 154(b) by 0 days.

(21) Appl. No.: 09/073,213

(22) Filed: May 4, 1998

(51) Int. Cl.$^7$ .................................................. G01N 33/533

(52) U.S. Cl. ............................. 435/7.23; 435/4; 435/7.1; 435/7.2; 530/387.1; 530/388.1; 530/388.8; 530/388.85; 530/391.3

(58) Field of Search .......................... 530/388.85, 388.1, 530/387.1, 388.8, 391.3; 424/156.1, 155.1, 145.1, 179.1; 435/7.23, 326, 344.1, 344, 7.1, 7.2, 4

(56) References Cited

U.S. PATENT DOCUMENTS

| | | |
|---|---|---|
| 5,162,504 | 11/1992 | Horoszewicz . |
| 5,474,903 | 12/1995 | Huland . |
| 5,489,525 | 2/1996 | Pastan . |
| 5,688,658 | 11/1997 | Diamandis . |
| 5,741,648 | 4/1998 | Hemstreet, III et al. . |
| 5,935,818 | * 8/1999 | Israel et al. . |

FOREIGN PATENT DOCUMENTS

WO 98/03873    1/1998  (WO) .

OTHER PUBLICATIONS

Barren, III, et al., 1997, The Prostate 30:65–68.
Brandt et al., 1996, "Isolation of single cancer cells and coherent cell sheets from peripheral blood of cancer patients with reference to shedded cytokeratin Aug. 18 and erbB–2 oncoprotein fragments", Proc. Am. Assn. Cancer Res. 37:80 (abstract 555).
Brandt et al., 1997, "Breast cancer metastasis: separation of double–positive cytokeratin/c–erbB–2–double positive single and clustered cells from peripheral blood of patients", Proc. Am. Assn. Cancer Res. 38:268 (abstract 1798).
Brandt et al., 1997, "Circulating prostate–specific antigen/CD14–double–positive cells: a biomarker indicating low risk for hematogeneous metastasis of prostate cancer", J. Natl. Cancer Inst. 89:174.
Gregorakis et al., 1998, "Prostate–specific membrane antigen: current and future utility", Sem. Urologic Oncology 16:2–12.
Murphy et al., 1998, "Current evaluation of the tissue localization and diagnostic utility of prostate specific membrane antigen", Cancer 83:2259–2269.

Murphy et al., 1996, "Measurement of prostate–specific membrane antigen in the serum with a new antibody", The Prostate 28:266–271.
Hamdy et al., 1992, British Journal of Urology 69:392–396.
Parks, D.R., 1986, "Flow cytometry and fluorescence activated cell sorting (FACS)", Chapter 29, in: *Handbook of Experimental Immunology*, vol. 1: Immunology, Weir et al. (eds.), Blackwell Scientific Publications, Boston MA, pp. 29.1–29.21.
Carter et al., 1996, "Prostate–specific membrane antigen is a hydrolase with substrate and pharmacologic characteristics of a neuropeptidase", PNAS USA, 93:749–753.
Catalona et al., 1996, "Evaluation of percentage of free serum prostate–specific antigen to improve specificity of prostate cancer screening", JAMA,274:1214–1220.
Doornbos et al., 1994, "Visible diode lasers can be used for flow cytometric immunofluorescence and DNA analysis", Cytometry, 15:267–271.
Gardiner, et al., 1996, "Abnormal prostatic cells in ejaculates from men with prostatic cancer—a preliminary report", British J. Urology, 78:414–418.
Glade et al., 1996, "Multiparameter flow cytometric characterization in epidermal cell suspensions prepared from normal and hyperproliferative human skin using optimized thermolysin–trypsin protocol", Arch. Dermatol. Res., 288:203–210.
Horoszewicz et al., 1987, "Monoclonal antibodies to a new antigenic marker in epithelial prostatic cells and serum of prostatic cancer patients", Anticancer Res., 7:927–935.
Hussain et al., 1996, "Prostate cancer: flow cytometric methods for detection of bone marrow micrometases", Cytochem. Comm. in Clinical Cytometry, 26:40–46.
Israeli et al., 1993, "Molecular cloning of a complementary DNA encoding a prostate–specific membrane antigen", Cancer Res., 53:227–230.
Israeli et al., 1994, "Expression of the prostate–specific membrane antigen", Cancer Res., 54:1807–1811.
Kaighn et al., 1979, "Establishment and characterization of a human prostatic carcinoma cell line (PC–3)", Invest. Urol., 17:16–23.
Keetch et al., 1994, "Serial prostatic biopsies in men with persistently elevated serum prostate specific antigen values", J. Urol., 151:1571–1574.

(List continued on next page.)

*Primary Examiner*—Sheela Huff
*Assistant Examiner*—Larry R. Helms
(74) *Attorney, Agent, or Firm*—Pennie & Edmonds LLP (57) ABSTRACT

The present invention is directed to methods of detecting prostate cancer in a sample of a body fluid with prostate cell marker-specific and epithelial cell marker-specific antibodies as well as to kits comprising such antibodies for use in the detection of prostate cancer. The present invention is also directed to methods of detecting prostate cancer in a sample of a body fluid with prostate cell marker-specific and tumor associated marker-specific antibodies as well as to kits comprising such antibodies for use in the detection of prostate cancer.

18 Claims, 6 Drawing Sheets

OTHER PUBLICATIONS

Kemmner et al., 1992, "Separation of tumor cells from a suspension of dissociated human colorectal carcinoma tissue by means of monoclonal antibody–coated magnetic beads", J. Immunol. Meth., 147:197–200.

Lilja, 1993, "Significance of different molecular forms of serum PSA", Urol. Clin. North Amer., 20(4):681–686.

Liu, H. et al., 1997, "Monoclonal antibodies to the extracellular domain of prostate–specific membrane antigen also react with tumor vascular endothelium", Cancer Res., 57:3629–3634.

Morrison et al., 1984, "Chimeric human antibody molecules: mouse antigen–binding domains with human constant region domains", PNAS USA, 81:6851–6855.

Murphy et al., 1996, "Evaluation and comparison of two new prostate carcinoma markers", Cancer, 78(4):809–818.

Murphy et al., 1995, "Comparison of prostate specific membrane antigen, and LNCaP–based enzyme–linked immunosorbent assays in prostatic cancer patients and patients with benign prostatic enlargement", Prostate, 26:164–168.

Murphy et al., 1995, "Comparison of prostate specific membrane antigen, and prostate specific antigen levels in prostatic cancer patients", Anticancer Res., 15:1473–1479.

Nelson et al., 1998, "An expressed–sequence–tag database of the human prostate: sequence analysis of 1168 cDNA clones", Genomics, 47:12–25.

Neuberger et al., 1984, "Recombinant antibodies possessing novel effector functions", Nature, 81:6851.

Oesterling et al., 1995, "Free, complexed and total serum prostate specific antigen: the establishment of appropriate reference ranges for their concentrations and ratios", J. Urol., 154:1090–1095.

Parker et al., 1997, "Cancer Statistcs, 1997", Cancer Abstracts, 47(1):5–27.

Racila et al., 1998, "Detection and characterization of carcinoma cells in the blood", PNAS USA, 95:4589–4594.

Reiter et al., 1998, "Prostate stem cell antigen: a cell surface marker overexpressed in prostate cancer", PNAS USA, 95:1735–1740.

Rochon et al., 1994, "Western blot assay for prostate–specific membrane antigen in serum of prostate cancer patients", Prostate, 25:219–223.

Shen et al., 1995, "Identification of the human prostatic carcinoma oncogene PTI–1 by rapid expression cloning and differential RNA display", PNAS USA, 92:6778–6782.

Toubert et al., 1996, "Percentage of free serum prostate–specific antigen: a new tool in the early diagnosis of prostatic cancer", Eur. J. Cancer, 32A(12):2088–2093.

van Hooijdonk et al., 1994, "TO–PRO–3 Iodide: a novel HeNe laser–excitable DNA stain as an alternative for propidium iodide in multiparameter flow cytometry", Cytometry, 17:185–189.

Zweig and Campbell, 1993, "Receiver–operating characteristic (ROC) plots: a fundamental evaluation tool in clinical medicine", Clin. Chem., 39(4):561–577.

Harlow et al., Antibodies, A Laboratory Manual, Cold Spring Harbor Laboratory, 1988.*

* cited by examiner

NON-INVASIVE METHODS TO DETECT PROSTATE CANCER

1. FIELD OF THE INVENTION

The present invention is directed to methods for the detection of prostate cancer in an individual by assessing prostate cells in a body fluid. The present invention is also related to commercial kits for use in the detection of prostate cancer.

2. BACKGROUND OF THE INVENTION

In the United States prostate cancer is first in absolute incidence with an estimated 210,000 new cases in 1997, and second to lung cancer for deaths with an estimated 41,800 deaths in 1997. Parker et al., 1997, Cancer Abstracts 47(1):5–27. The incidence of prostate cancer has risen at an average annual rate of 3% per annum from 1960 to 1985. Boyle, 1997, Proceedings—First International Consultation on Prostate Cancer. Prostate cancer affects older men with the rates of incidence for men in their 40's being 1–2 per 100,000, the rates for Caucasian men in their 80's 1,200 per 100,000 and for African American men 1,600 per 100,000. In 1900 only 25% of the United States population lived to the age of 65. Currently that number is 70%. Brody, 1985, Nature 315:463–466.

The guidelines for diagnosis of new prostate cancer adopted by the American Cancer Society in June 1997 recommends an annual prostate specific antigen (PSA) exam as well as a digital rectal exam (DRE) for men over 50 years of age and in certain instances over the age of 45. Further action should be taken only if one or both screening methodologies are abnormal. An abnormal PSA is defined as a PSA greater than 4.0 ng/ml.

Patients suspected of having prostate cancer based on a PSA test and a DRE, would then undergo additional radiographic and/or surgical tests to confirm diagnosis. These additional tests may include urology consultation, ultrasound and tissue biopsy with pathological evaluation. The cost associated with these confirmatory tests typically exceeds $5000.

The PSA test and DRE are acceptable screening methods but one of the short comings of these screening methods is the large number of falsely identified patients. A PSA European screening study biopsied 976 men and detected 190 cases of prostate cancer. 767 of the 976 men had either of both a PSA value in the range of 4 to 10 ng/ml or a suspect DRE. Of these 767 patients, only 177 had prostate cancer. 77% of the population did not have prostate cancer. Schröder, 1997, First International Consultation on Prostate Cancer, 179–210.

Final determination of prostate cancer must be made with more expensive and invasive biopsy. However, even a single biopsy can miss prostate cancer. In one third of patients who underwent a serial biopsy study, multiple biopsies were required for the detection of prostate cancer. Keetch et al., 1994, J. Urol. 151:1571–1574.

A recent methodology attempted to further identify patients who are at risk for prostate cancer has been the determination of percent free PSA. Murphy et al., 1996, Cancer 78(4):809–818, report a difference in the ratio of free PSA to total PSA in 226 patients with benign prostatic hyperplasia and patients with no evidence of disease compared to the same ratio in patients with biopsy-proven prostate cancer. The ratio was 12.1% in patients with no evidence of prostate cancer and in the prostate cancer group the ratio was 7.1%. Despite the differences observed, the authors concluded that their data suggest that free PSA values do not provide additional diagnostic benefit compared to total PSA in screening populations in the presence of suspected cancer, post prostatectomy or in metastatic disease. Pronounced differences in the ability of available assays to detect free PSA have generated multiple cutoffs, ranging from 15–20%. Catalona et al., 1996, JAMA 274:1214–1220; Oesterling et al., 1995, J. Urol. 154:1090–1095; Toubert et al., 1996, Eur. J. Cancer 32A (12):2088–2093; Lilja, 1993, Urol. Clin. North Am. 20(4):681–686. Regardless of the potential sensitivity gained, prostate cancer will have to be confirmed with a cytological assessment. Clearly, the development of a non-invasive, cytologically based assay, able to compliment the traditional PSA and DRE, would assist the clinician in the early detection and treatment of prostate cancer without the necessity of relying on more expensive invasive means.

Citation or identification of any reference in Section 2 or any other section of this application shall not be construed as an admission that such reference is available as prior art to the present invention.

3. SUMMARY OF THE INVENTION

The present invention is directed to a method for the detection of prostate cancer comprising comparing the ratio of the number of prostate cells and the total number of epithelial cells in a body fluid sample, in which the ratio is elevated in individuals with prostate cancer as compared to individuals free of prostate cancer. The ratio is determined by (1) quantifying the number of prostate cells in a body fluid sample; (2) quantifying the total number of epithelial cells in the fluid sample; and (3) calculating the ratio of the number of prostate cells to the total number of epithelial cells. In an aspect of this embodiment of the present invention, the prostate cells are quantified by using an antibody which is specific for a prostate cell-specific marker, such as the prostate specific antigen (PSA) or the prostate specific membrane antigen (PSMA). In a preferred aspect, the prostate cell-specific marker is PSMA. The body fluid can be, but is not limited to, blood, urine or semen. In a preferred aspect, the body fluid is semen.

The present invention is also directed to a method for the detection of prostate cancer comprising comparing the ratio of the number of prostate cells which express a tumor associated marker and the total number of prostate cells in a body fluid sample, in which the ratio is elevated in individuals with prostate cancer as compared to individuals free of prostate cancer. The ratio is determined by (1) quantifying the total number of prostate cells in a body fluid sample; (2) quantifying the number of prostate cells in the fluid sample which express a tumor associated marker; and (3) calculating the ratio of the number of prostate cells which express the marker to the total number of prostate cells. In an aspect of this embodiment of the present invention, the prostate cells are quantified by using an antibody which is specific for a prostate cell-specific marker, such as the prostate specific antigen (PSA) or the prostate specific membrane antigen (PSMA). In a preferred aspect of this embodiment, the prostate cell-specific marker is PSMA. The body fluid can be, but is not limited to, blood, urine or semen. In a preferred aspect, the body fluid is semen.

The present invention is also directed to commercial kits for the detection of prostate cancer which comprise a prostate cell marker-specific antibody and an epithelial cell marker-specific antibody in one or more containers.

Alternatively, the commercial kits comprise a prostate cell marker-specific antibody and a tumor associated marker-specific antibody in one or more containers.

As used herein, the term "epithelial cell marker" refers to an epithelial cell marker not present on sperm cells.

As used herein, the term "prostate cell-specific antibody" refers to any polyclonal or monoclonal antibody, or portion thereof, that can immunospecifically bind to an epitope present on or in a prostate cell. For example, such an antibody immunospecifically binds to PSMA or binds to an extracellular portion or to an intracellular portion of PSMA.

As used herein, the term "tumor associated marker-specific antibody" refers to any polyclonal or monoclonal antibody, or portion thereof, that can immunospecifically bind to a tumor associated marker, which when expressed in or on a cell is indicative that such cell is cancerous.

The invention may be understood more fully by reference to the following brief description of the figures, detailed description, illustrative, non-limiting examples and the appended figures.

4. BRIEF DESCRIPTION OF THE FIGURES

In FIG. 6A the PSMA antibody is coupled to the dye r-phycoerythrin (PE) via a strepavidin-biotin bridge and the DNA stain used was To-Pro 3. In FIG. 6B the PSMA antibody is linked to an alternative fluorochrome, Phycobilisome-3, and the DNA stain used was Po-Pro 3.

5. DETAILED DESCRIPTION OF THE INVENTION

The present invention is based, in part, on the discovery that the ratio of prostate cells to total epithelial cells present in a body fluid sample is different in subjects having prostate cancer as compared to those subjects who are free of prostate cancer. The present invention is also based, in part, on the discovery that the ratio of prostate cells expressing a tumor associated marker to total prostate cells present in a body fluid sample is different in subjects having prostate cancer as compared to those subjects who are free of prostate cancer.

An embodiment of the present invention is directed to a method for the detection of prostate cancer comprising determining the ratio of the number of prostate cells and the total number of epithelial cells in a body fluid sample, in which the ratio is elevated in individuals with prostate cancer as compared to individuals free of prostate cancer. The ratio is determined by (1) quantifying the number of prostate cells in a body fluid sample; (2) quantifying the total number of epithelial cells in the fluid sample; and (3) calculating the ratio of the number of prostate cells to the total number of epithelial cells. The calculated ratio will range from 0 to 1 and the "cut value" above which an individual is classified as having prostate cancer is the ratio at which the assay is at its maximum sensitivity and specificity. The sensitivity and specificity of an assay can be calculated using a Receiver-operating characteristic (ROC) plot, which provides an index of accuracy by demonstrating the limits of a test's ability to discriminate between alternative states of health over the complete spectrum of operating conditions. For a general review of ROC plots, see Zweig and Campbell, 1993, Clin. Chem. 39/4:561–577 which is incorporated by reference herein in its entirety. A ROC graph is a plot of all the sensitivity/specificity pairs resulting from continuously varying the decision threshold over the entire range of results observed. In each case, the ROC plot depicts the overlap between the two distributions by plotting the sensitivity vs 1-specificity for the complete range of decision thresholds. See Zweig and Campbell, supra, especially at page 564, column 2 to page 565, column 1.

In an illustrative example set forth below, see Section 6, in individuals free of prostate cancer, the ratio was calculated to be about 0.024 to about 0.38, with a mean of 0.11; in individuals with prostate cancer, the ratio was calculated to be about 0.121 to about 0.994, with a mean of 0.57. In this illustrative example, the "cut value" above which an individual is classified positive was 0.21. The cut value was determined using a Receiver-operating characteristic plot and is the point at which the specificity and sensitivity curves intersect, i.e., the point of maximum specificity and maximum sensitivity.

An alternative embodiment of the present invention is directed to a method for the detection of prostate cancer comprising determining the ratio of the number of prostate cells which express a tumor associated marker and the total number of prostate cells in a body fluid sample, in which the ratio is elevated in individuals with prostate cancer as compared to individuals free of prostate cancer. The ratio is determined by (1) quantifying the total number of prostate cells in a body fluid sample; (2) quantifying the number of prostate cells in the fluid sample which express a tumor associated marker; and (3) calculating the ratio of the number of prostate cells expressing the marker to the total number of prostate cells. The calculated ratio will range from 0 to 1 and the "cut value" above which an individual is classified as having prostate cancer is the ratio at which the assay is at its maximum sensitivity and specificity. The sensitivity and specificity of an assay can be calculated using a Receiver-operating characteristic (ROC) plot as described in the preceding paragraphs above.

5.1 DETERMINING OF PROSTATE AND TOTAL EPITHELIAL CELLS

The cells used in this detection assay can be obtained from any body fluid that contains prostate cells, such as blood, urine or semen. A collected sample of body fluid can be processed before determining the number of prostate cells and the total number of epithelial cells. For example, when the cells are obtained from blood, the red blood cells can first be removed, for example, through gravity centrifugation over a Ficoll-hypaque gradient.

The prostate and epithelial cells can be detected and quantified by any method known to those of skill in the art. For example, prostate cells can be detected and quantified using an antibody specific for a prostate cell-specific marker or using a fragment comprising the binding domain of an antibody specific for a prostate cell marker. Epithelial cells can be detected and quantified using an antibody specific for an epithelial cell-specific marker. Preferably, in this aspect of the invention, the antibodies used for detection and quantification are monoclonal antibodies.

Prostate cell-specific markers are known and include prostate-specific antigen (PSA), prostate-specific membrane antigen (PSMA), prostate secretory protein (PSP), prostate acid phosphatase (PAP), and human glandular kallekrein 2 (HK-2). Another prostate cell-specific marker is prostate stem cell antigen (PSCA) identified by Reiter et al., 1998, Proc. Natl. Acad. Sci. USA 95:1735–1740. Yet another prostate cell-specific marker is PTI-1, a prostate carcinoma oncogene identified by Shen et al., 1995, Proc. Natl. Acad. Sci. USA 92:6778–6782. For a general review of prostate cell-specific markers, see Nelson et al., 1998, Genomics 47:12–25.

In a preferred aspect of this embodiment of the invention, the prostate cells are quantitated by using a monoclonal antibody specific for PSMA. PSMA is a 120 kDa molecular weight protein expressed in prostate tissues and was originally identified by reactivity with a monoclonal antibody designated 7E11-C5. Horoszewicz et al., 1987, Anticancer Res. 7:927–935; U.S. Pat. No. 5,162,504. PSMA was obtained in purified form (Wright et al., 1990, *Antibody Immunoconjugates and Radio Pharmaceuticals* 3:Abstract 193) and characterized as a type II transmembrane protein having some sequence identity with the transferrin receptor (Israeli et al., 1994, Cancer Res. 54:1807–1811) and with NAALADase activity (Carter et al., 1996, Proc. Natl. Acad. Sci. USA 93:749–753). More importantly, although PSMA is expressed in normal prostate, benign prostate hyperplasia and prostate cancer, PSMA is expressed in increased amounts in prostate cancer, and an elevated level of PSMA is also detectable in the sera of these prostate cancer patients. Horoszewicz et al., 1987, supra; Rochon et al., 1994, Prostate 25:219–223; Murphy et al., 1995, Prostate 26:164–168; and Murphy et al., 1995, Anticancer Res. 15:1473–1479. A cDNA encoding PSMA has been cloned. Israeli et al., 1993, Cancer Res. 53:227–230.

PSMA-specific antibodies are known and include 7E11.C5 (ATCC Accession No. HB10494); 3F5.4G6 (ATCC Accession No. HB12060); 3D7-1.1 (ATCC Accession No. HB12309); 4E10-1.14 (ATCC Accession No. HB12310); 1G3 (ATCC Accession No. HB12489); 1G9 (ATCC Accession No. HB-12495); 2C7 (ATCC Accession No. HB-12490); 3C4 (ATCC Accession No. HB-12494); 3C6 (ATCC Accession No. HB-12491); 3C9 (ATCC Accession No. HB-12484); 3E6 (ATCC Accession No. HB-12486); 3E11 (ATCC Accession No. HB-12488); 3G6 (ATCC Accession No. 12485); 4D4 (ATCC Accession No. HB-12493); 4D8 (ATCC Accession No. HB12487); or 4C8B9 (ATCC Accession No. HB-12492), see WO 97/35616. Other PSMA-specific antibodies which can be employed in the present invention include E99 (ATCC Accession No. HB-12101); J415 (ATCC Accession No. HB-12109); J533 (ATCC Accession No. HB-12127); and J591 (ATCC Accession No. HB12126), each isolated by Bander, International Patent Publication WO 98/03873. Additional non-limiting examples of antibodies specific for PSMA, which can be used in the methods of the present invention, are presented in Table I. All the antibodies presented in Table I are murine IgG monoclonal antibodies, which are reactive to native PSMA. The approximate location of the binding epitope of each antibody, as well as the isotype subclass of each antibody, is also summarized in Table I.

TABLE I

Binding Specificity and Isotype of PSMA-Specific Antibodies to Native PSMA and PSMA Fragments

| Antibody | Native PSMA | 1–173 | 134–437 | 437–750 | Isotype[a] |
|---|---|---|---|---|---|
| 3F6 | + | – | – | – | $IgG_{2b}$ |
| 2E4 | + | weak | – | – | $IgG_{2a}$ |
| 3C2 | + | + | + | – | $IgG_{2a}$ |
| 4C8G8 | + | – | + | – | $IgG_{2b}$ |
| 2C4 | + | – | + | – | $IgG_1$ |
| 4C11 | + | – | + | – | $IgG_1$ |
| 1D11 | + | – | + | – | $IgG_{2b}$ |
| 4E8 | + | – | + | – | $IgG_{2b}$ |
| 2G5 | + | – | + | – | $IgG_{2b}$ |
| 4E6 | + | – | + | – | $IgG_1$ |
| 1F4 | + | – | + | – | $IgG_1$ |
| 2E3 | + | – | – | + | $IgG_{2a}$ |
| 3D8 | + | – | – | + | $IgG_{2a}$ |
| 4F8 | + | – | – | + | $IgG_{2a}$ |
| 3D2 | + | – | – | + | $IgG_{2a}$ |
| 1G7 | + | – | – | + | $IgG_{2a}$ |
| 3D4 | + | – | – | + | $IgG_{2a}$ |
| 4D4 | + | – | – | – | $IgG_1$ |
| 5G10 | + | – | + | – | $IgG_1$ |
| 5E9 | + | – | + | – | $IgG_1$ |

[a]Isotype specificity was determined using IsoStrip tests (Boehringer-Manheim) for murine antibody isotype determinations which were conducted according to manufacturer's instructions.

In an alternative aspect of this embodiment of the invention, prostate cells are quantitated using a monoclonal antibody specific for a prostate cell-specific marker selected from the group consisting of prostate-specific antigen (PSA), prostate secretory protein (PSP), prostate acid phosphatase (PAP), human glandular kallekrein 2 (HK-2), prostate stem cell antigen (PSCA), and PTI-1.

In yet another alternative aspect of this embodiment, prostate cells are quantitated using the PR-1 monoclonal antibody (ATCC Accession No. HB-11145; Pastan, U.S. Pat. No. 5,489,525).

Epithelial cell-specific markers are known and include cytokeratin and epithelial cell adhesion molecule (EPCAM). The monoclonal antibody CAM 5.2 is specific for cytokeratin and is useful in the methods of the present invention for the quantification of the total number of epithelial cells in a body fluid sample. Other cytokeratin-specific antibodies include 5D3 and LP34 (NovoCastra, Newcastle, UK), TS-1, NCL-5D3 (PharMingen, San Diego, Calif.), UCD/Ab6.11, UCD/Ab6.01 and UCD/Ab10.11 (American Type Culture Collection, Manassas, Va.). Antibody GA73.3 EPCAM, which binds to EPCAM, is also useful in the methods of the present invention for the quantification of epithelial cells in a body fluid sample.

Further, a portion of an antibody specific for a prostate cell marker or an epithelial cell marker, including purified fragments of the monoclonal antibodies having at least a portion of an antigen binding region, including such as Fv, $F(ab')_2$, Fab fragments (Harlow and Lane, 1988, Antibody, Cold Spring Harbor), single chain antibodies (U.S. Pat. No. 4,946,778), chimeric or humanized antibodies (Morrison et al., 1984, Proc. Natl. Acad. Sci. USA 81:6851; Neuberger et al., 1984 Nature 315: 604–608) and complementarity determining regions (CDR) can be used in the present invention. Mimetics of the antibodies can also be used in the present invention.

The prostate cell marker-specific or epithelial cell marker-specific antibody or portion thereof can, in turn, be detected by having the antibody labeled directly or indirectly with a detectable marker. Alternatively, the prostate cell marker-specific or epithelial cell marker-specific antibody ("first antibody") can be contacted with a second antibody which is specific for the prostate cell marker-specific antibody or the epithelial cell marker-specific antibody, respectively. This second antibody can be labeled directly or indirectly with a detectable marker. Such detectable markers include, but are not limited to, a radioactive moiety, a substrate converting enzyme, fluorescent marker, biotin, and the like. For a general review, see, *Antibodies A Laboratory Manual*, 1988, Harlow et al., Cold Spring Harbor Laboratory Press, Cold Spring Harbor, N.Y.

Once the number of prostate and epithelial cells in the sample has been determined, a prostate cell:epithelial cell ratio can be calculated and used to determine if the subject who provided the sample has prostate cancer. Alternatively, the ratio can be used in conjunction with other tests, e.g., DRE, PSA, to determine if the subject who provided the sample has prostate cancer. The ratio can also be used to follow the progression of the disease as the patient is being treated. See the discussion in Section 6.3 and FIGS. 4A and 4B, infra.

In a preferred aspect of this embodiment of the invention, the prostate and epithelial cells can be detected and quantified using a flow cytometer. Fluorescence activated cell sorting (FACS) flow cytometry is a common technique for antibody based cell detection and separation. Typically, detection and separation by flow cytometry is performed as follows. A sample containing the cells of interest is contacted with fluorochrome-conjugated antibodies, which allows for the binding of the antibodies to the specific cell marker, such as PSMA. The bound cells are then washed by one or more centrifugation and resuspension steps. The cells are then run through a FACS which separates the cells based on the different fluorescence characteristics imparted by the cell-bound fluorochrome. FACS systems are available in varying levels of performance and ability, including multi-color analysis which is preferred in the resent invention. For a general review of flow cytometry, see Parks et al., 1986, Chapter 29:Flow Cytometry and fluorescence activated cell sorting (FACS) in: *Handbook of Experimental Immunology*, Volume 1:Immunochemistry, Weir et al. (eds.), Blackwell Scientific Publications, Boston, Mass.

In one aspect of this embodiment of the present invention, cells in a body fluid sample are first contacted with an antibody specific to a prostate cell-specific marker and with an antibody that is specific for an epithelial cell-specific marker, which epithelial marker is not present on sperm cells. These "first" antibodies can be labeled either directly or indirectly with, e.g., a fluorescent marker or a biotin. Alternatively, these "first" antibodies can be reacted with a "second" antibody which is specific for the first antibody, and which second antibody is labeled either directly or indirectly with, e.g., a fluorescent marker. In another aspect, the "first" antibody, which is specific for PSMA, is directly labeled with biotin and the "second" antibody, which is specific for biotin, is directly labeled with a fluorescent marker; the "first" antibody, which is specific for the epithelial cell marker, is indirectly labeled with a fluorescent marker. The antibody-contacted cells are then assayed in a flow cytometer.

The fluorescent label associated with the prostate cells and the fluorescent label associated with the epithelial cells need to fluoresce at different wavelengths, such that the prostate cells and the epithelial cells can be distinguished. The fluorescence detected by the flow cytometer at the respective different wavelengths allows for the determination of the number of prostate and total epithelial cells in the sample by the characteristic profile of forward and side scatter of the cells based on their fluorescence. Once the number of prostate and epithelial cells in the sample has been determined, a prostate cell:epithelial cell ratio can be calculated and used to determine if the subject who provided the sample has prostate cancer. Alternatively, the ratio can be used in conjunction with other tests, e.g., DRE, PSA, to determine if the subject who provided the sample has prostate cancer.

In one aspect of this embodiment of the invention, when the body fluid is semen, the cells from such semen sample can be stained with a fluorescent dye specific for DNA, such that the haploid sperm cells can be distinguished from the diploid prostate and epithelial cells. The haploid cells can then be removed from analysis by specific gating, i.e., DNA signal histogram. However, DNA staining of the cell sample is not always necessary and may depend on the sample in terms of the number of cells and the quality of the sample, such as the number of cells present. Moreover, if the sperm cells are distinguished and controlled for, any epithelial cell marker, including those expressed on sperm cells, can be used in the present invention.

Other detection and separation techniques besides flow cytometry can also provide for the determination of the number of prostate and epithelial cells in a fast manner. One such method is biotin-avidin based separation by affinity chromatography. Typically, such a technique is performed by incubating the sample of cells with biotin-conjugated antibodies to specific markers, such as PSMA and cytokeratin, followed by passage through an avidin column. Biotin-antibody-cell complexes bind to the column via the biotin-avidin interaction, while other cells pass through the column. The specificity of the biotin-avidin system is well suited for rapid positive detection and separation. Once isolated, the prostate and epithelial cells can be quantified and the prostate cell:epithelial cell ratio calculated. The calculated ratio can be used to determine if the subject who provided the sample has prostate cancer. Alternatively, the ratio can be used in conjunction with other tests, e.g., DRE, PSA, can be used to determine if the subject who provided the sample has prostate cancer.

Yet another method is magnetic separation using antibody-coated magnetic beads. Kemmner et al., 1992, J. Immunol. Methods 147:197–200; Racila et al., 1998, Proc. Natl. Acad. Sci. USA 95:4589–4594.

5.2 DETERMINATION OF PROSTATE CELLS EXPRESSING A TUMOR ASSOCIATED MARKER AND TOTAL PROSTATE CELLS

The cells used in this detection assay can be obtained from any body fluid that contains prostate cells, such as blood, urine or semen. A collected sample of body fluid can be processed before determining the total number of prostate cells and the number of prostate cells which express a tumor associated marker. For example, when the cells are obtained from blood, the red blood cells can first be removed, for example, through gravity centrifugation over a Ficoll-hypaque gradient.

The prostate cells can be detected and quantified by any method known to those of skill in the art. For example, prostate cells can be detected and quantified using an antibody specific for a prostate cell-specific marker or using a fragment comprising the binding domain of an antibody specific for a prostate cell marker. The prostate cells expressing a tumor associated marker can be detected and quantified using an antibody specific for a prostate cell-specific marker or using a fragment comprising the binding domain of an antibody specific for a prostate cell marker and a tumor associated marker-specific antibody or a fragment of the antibody. The prostate cells expressing a tumor associated marker can also be detected and quantified by using only a tumor associated marker-specific antibody on a prostate cell population already identified by a prostate cell marker-specific antibody. Preferably, the antibodies used for detection and quantification are monoclonal antibodies.

Prostate cell-specific markers and antibodies which bind thereto are known and are described in Section 5.1, supra. In a preferred aspect of this embodiment of the invention, the prostate cells are quantitated by using a monoclonal antibody specific for PSMA, which antibodies are described in Section 5.1, supra.

In an alternative aspect of this embodiment of the invention, prostate cells are quantitated using a monoclonal antibody specific for a prostate cell-specific marker selected from the group consisting of prostate-specific antigen (PSA), prostate secretory protein (PSP), prostate acid phosphatase (PAP), human glandular kallekrein 2 (HK-2), prostate stem cell antigen (PSCA), and PTI-1.

In yet another alternative aspect of this embodiment, prostate cells are quantitated using the PR-1 monoclonal antibody (ATCC Accession No. HB-11145; Pastan, U.S. Pat. No. 5,489,525).

Tumor associated markers are known and include those markers which when expressed in or on a cell are indicative that such cell is cancerous. Such markers include mutant p53, mutant Rb, fos, jun, her2, neu, yes, ras, mutant Notch, and the like. In addition, antibodies to these tumor associated markers are known and any such antibody is useful in the methods and kits of the present invention.

Further, a portion of an antibody specific for a prostate cell marker or a tumor associated marker, including purified fragments of the monoclonal antibodies having at least a portion of an antigen binding region, including such as Fv, $F(ab')_2$, Fab fragments (Harlow and Lane, 1988, Antibody, Cold Spring Harbor), single chain antibodies (U.S. Pat. No. 4,946,778), chimeric or humanized antibodies (Morrison et al., 1984, Proc. Natl. Acad. Sci. USA 81:6851; Neuberger et al., 1984 Nature 312:604–608) and complementarity determining regions (CDR) can be used in the present invention. Mimetics of the antibodies can also be used in the present invention.

The prostate cell marker-specific or tumor associated marker-specific antibody or portion thereof can, in turn, be detected by having the antibody labeled directly or indirectly with a detectable marker. Alternatively, the prostate cell marker-specific or tumor associated marker-specific antibody ("first antibody") can be contacted with a second antibody which is specific for the prostate cell marker-specific antibody or the tumor associated marker-specific antibody, respectively. This second antibody can be labeled directly or indirectly with a detectable marker. Such detectable markers include, but are not limited to, a radioactive moiety, a substrate converting enzyme, fluorescent marker, biotin, and the like. For a general review, see, *Antibodies, A Laboratory Manual*, 1988, Harlow et al., Cold Spring Harbor Laboratory Press, Cold Spring Harbor, N.Y.

Once the total number of prostate cell and prostate cell expressing a tumor associated marker (prostate cell/tumor marker+) in the sample has been determined, a prostate cell/tumor cell marker+:total prostate cell ratio can be calculated and used to determine if the subject who provided the sample has prostate cancer. Alternatively, the ratio can be used in conjunction with other tests, e.g., DRE, PSA, can be used to determine if the subject who provided the sample has prostate cancer. The ratio can also be used to follow the progression of the disease as the patient is being treated.

In a preferred aspect of this embodiment of the invention, the prostate cells and prostate cells expressing a tumor associated marker can be detected and quantified using a flow cytometer. In this aspect of the present invention, cells in a body fluid sample are first contacted with an antibody specific to a prostate cell-specific marker and with an antibody that is specific for a tumor associated marker. These "first" antibodies can be labeled either directly or indirectly with, e.g., a fluorescent marker or a biotin. Alternatively, these "first" antibodies can be reacted with a "second" antibody which is specific for the first antibody, and which second antibody is labeled either directly or indirectly with, e.g., a fluorescent marker. In another aspect, the "first" antibody, which is specific for PSMA, is directly labeled with biotin and the "second" antibody, which is specific for biotin, is directly labeled with a fluorescent marker; the "first" antibody, which is specific for the tumor associated marker, is indirectly labeled with a fluorescent marker. The antibody-contacted cells are then assayed in a flow cytometer.

The fluorescent label associated with the prostate cell marker and the fluorescent label associated with the tumor associated marker need to fluoresce at different wavelengths, such that prostate cells and prostate cells expressing the tumor associated marker can be distinguished. The fluorescence detected by the flow cytometer at the respective different wavelengths allows for the determination of the total number of prostate cells and the number of prostate cells expressing a tumor associated marker in the sample by the characteristic profile of forward and side scatter of the cells based on their fluorescence. Once the total number of prostate cells and prostate cells expressing a tumor associated marker (prostate cell/tumor marker+) in the sample has been determined, a prostate cell/tumor marker+:prostate cell ratio can be calculated and used to determine if the subject who provided the sample has prostate cancer. Alternatively, the ratio can be used in conjunction with other tests, e.g., DRE, PSA, to determine if the subject who provided the sample has prostate cancer.

In one aspect of this embodiment of the invention, when the body fluid is semen, the cells from such semen sample can be stained with a fluorescent dye specific for DNA, such that the haploid sperm cells can be distinguished from the diploid prostate cells. The haploid cells can then be removed from analysis by specific gating, i.e., DNA signal histogram. However, DNA staining of the cell sample is not always necessary and may depend on the sample in terms of the number of cells and the quality of the sample, such as the number of cells present.

Other detection and separation techniques besides flow cytometry can also provide for the determination of the number of prostate cells and prostate cells expressing a tumor associated marker in a fast manner. One such method is biotin-avidin based separation by affinity chromatography. Typically, such a technique is performed by incubating the sample of cells with biotin-conjugated antibodies to specific markers, for example, PSMA and an antibody specific for mutant p53, followed by passage through an avidin column. Biotin-antibody-cell complexes bind to the column via the biotin-avidin interaction, while other cells pass through the column. The specificity of the biotin-avidin system is well suited for rapid positive detection and separation. Once isolated, the prostate cells and prostate cells expressing a tumor associated marker (prostate cell/tumor marker+) can be quantified and the prostate cell/tumor marker+:prostate cell ratio calculated. The calculated ratio can be used to determine if the subject who provided the sample has prostate cancer. Alternatively, the ratio can be used in conjunction with other tests, e.g., DRE, PSA, to determine if the subject who provided the sample has prostate cancer.

Yet another method is magnetic separation using antibody-coated magnetic beads. Kemmner et al., 1992, J. Immunol. Methods 147:197–200; Racila et al., 1998, Proc. Natl. Acad. Sci. USA 95:4589–4594.

5.3. KITS

One embodiment of the present invention encompasses kits containing prostate cell marker-specific and epithelial cell marker-specific antibodies in one or more containers for use in detecting the presence of prostate cancer. An alternative embodiment of the present invention encompasses kits containing prostate cell marker-specific and tumor associated marker-specific antibodies in one or more containers for use in detecting the presence of prostate cancer.

The antibodies can be formulated with acceptable carriers such that they can be used directly from the container without further preparation. Further, the antibodies can be lyophilized with lyoprotective agents known in the art, such as trehalose and tricine, for long term stability and shelf-life of the kit. Also, the antibody container(s) can be presented in a pack or dispenser device. The pack or dispenser device can be accompanied by instructions for use of the antibodies for detecting prostate cancer and for determining the ratio of prostate cells to epithelial cells or prostate cells expressing a tumor associated marker to total prostate cells, as well as instructions for determining the "cut value". Associated with such pack or dispenser device(s) can be a notice in the form prescribed by a governmental agency regulating the manufacture, use or sale of pharmaceuticals or biological products, which notice reflects approval by the agency of manufacture and use for diagnosis of human disease. The kits can further comprise other materials necessary to conducting the assay, such as control cell samples or manufactured fluorescent beads for calibrating the flow cytometer.

The following series of examples are presented by way of illustration and not by way of limitation on the scope of the invention.

6. EXAMPLE: DETERMINATION OF THE RATIO OF PROSTATE CELLS TO EPITHELIAL CELLS IN SEMEN

The following experiment demonstrates that the ratio of prostate cells to total epithelial cells is significantly different in subjects having prostate cancer as compared to those subjects free of prostate cancer.

6.1 MATERIALS AND METHODS

The samples used came from two types of patients, those with prostate cancer, or those without evidence of disease. Fifteen normal semen samples were obtained from a population with a median age of 33.1 years (range 25–55 years). A total of eleven prostate cancer patients provided sixteen semen samples. Two cancer patients provided multiple samples for the purpose of individual follow-up evaluation. Each cancer patient had biopsy proven prostate cancer with an elevated PSA ranging from 4.0 to 25 ng/ml. The cancer patient selection was made from a population with a median age of 60 years (range 45 to 65 years). All patients were staged using the TNM system. Sobin and Wittekind, 1997, TNM Classification of Malignant Tumors, Fifth Ed., Wiley-Liss, pub., New York, New York. Table II presents the clinical stage, age range, median age, and number of each class of samples of this population.

TABLE II

Classification of the Patient Samples

| | Prostate Cancer | | | | |
|---|---|---|---|---|---|
| | T1a | T1c | T2a | BPH | No Disease |
| Number of samples | 6 | 5 | 5 | 1 | 15 |
| Number of patients | 2 | 4 | 5 | 1 | 15 |
| Age range | 45–65 yrs | | 25–55 yrs | | |
| Median age | 60 yrs | | 33 yrs | | |

All samples were delivered promptly to our facility within one hour following ejaculation. Each sampling was initially incubated for a period of one hour at 37° C. to liquefy the specimen. Ten milliliters of RPMI media, warmed to 37° C. was added to the liquified semen, followed by centrifugation of the sample for 5 minutes at 400×G to collect the cells. The cell pellets were re-suspended in 1 ml of cold Phosphate Buffered Saline (PBS, 2.7 mM KCl, 7 mM $Na_2HPO_4$, 1.5 mM $KH_2PO_4$, 0.14 M NaCl, pH=7.4) and 2 ml of deionized water. Five milliliters of 80% ethanol fixative (Sigma Chemical Company, St. Louis, Mo.) was added to the cell suspension drop wise while vortexing to a final concentration of 50% ethanol.

Cell cultures of PNCF 007, PC-3, and LNCAP, were maintained in RPMI supplemented with 10% fetal calf sera in a $CO_2$ controlled incubator. PNCF 007 is a primary fibroblast cell line derived from a radical prostatectomy specimen developed at the Pacific Northwest Cancer Foundation. Characterization of this cell line has shown it to be negative for PSMA, as well as cytokeratin 8 and 18. The PC-3 cell line was purchased from American Type Culture Collection (ATCC, Rockville, Md.). This cell line was derived from a grade IV prostatic adenocarcinoma. The PC-3 cell line has been shown to be positive for cytokeratin 8 and 18 (Kaighn et al., 1979, Invest. Urol. 17:16–23) but negative for PSMA (Rochon et al., 1994, Prostate 25:219–223). LNCAP cells were purchased from ATCC (Rockville, Md.). LNCAP is a cell line developed from a secondary tumor extracted from the lymph node of a hormone refractory prostate cancer patient. Horoszewicz et al., 1980, Prog. Clin. Biol. Res. 37:115–132; Horoszewicz et al., 1983, Cancer Res. 43:1809–1818. The LNCAP cell line has been shown to be positive for both cytokeratin 8 and 18 and PSMA. Hussain et al., 1996, Cytometry Communications in Clinical Cytometry 26:40–46; Horoszewicz et al., 1987, Anticancer Res. 7:927–935. Cells were grown in monolayer to confluence and harvested with 0.02% EDTA in PBS. Cells were fixed in 50% ethanol as described previously and stored at −20° C. until stained.

The reagents used in this experiment and their functions are outlined in Table III.

TABLE III

| Reagents | Purpose |
| --- | --- |
| Antibodies | |
| 1) 7E11.C5 | 1) Antibody to Prostate Specific Membrane Antigen (PSMA). 7E11.C5 stains normal prostate cells and prostate cancer cells. |
| 2) CAM 5.2 | 2) Antibody to Cytokeratin 8 and 18. CAM 5.2 staining differentiates prostate luminal epithelial cells from basal cells. CAM 5.2 stains all primary prostate tumors. |
| 3) 399 | 3) Antibody to Prostate Specific Antigen (PSA). This antibody was used to identify prostate cells by PSA expression. |
| 4) KLH | 4) Antibody to Keyhole Limpet Hemocyanin, a control for non-discriminate staining. |
| Other Reagents | |
| 1) To-Pro 3 | 1) A DNA Stain with an absorption max at 642 nm and an emission maximum at 660 nm. This stain was detected in the FL-4 detector. |
| 2) Po-Pro 3 | 2) A DNA Stain with an absorption max at 539 nm and an emission maximum at 567 nm. This stain was detected in the FL-2 detector. |

TABLE III-continued

| Reagents | Purpose |
| --- | --- |
| 3) Streptavidin Phycoerythrin (PE) | 3) Used to report biotin Ab 7E11.C5 or Ab 399, its absorbance maximum is 480 nm and 578 nm and its emission maximum is 578 nm. This stain was detected in the FL-2 detector. |
| 4) Fluorescein Isothiocyanate (FITC) | 4) Directly labeled to CAM 5.2 and KLH, its absorbance maximum is 480 nm and 578 nm and its emission maximum is 578 nm. This stain was detected in the FL-1 detector. |
| 5) Phycobilisome-3 (PBXL-3) | 5) A fluorescent pigment from cyanobacteria. PBXL-3 was directly labeled to 7E11. The absorbance maximum is 614 nm and its emission maximum is 662 nm. This stain was detected in the FL-4 detector. |

The 7E11.C5 and the anti-PSA antibody 399 (a gift from Hybritech Incorporated, San Diego, Calif.) were biotinylated using the Pierce biotinylation kit (Pierce Chemical Co., Rockford, Ill.). Commercial phycoerythrin conjugated to streptavidin (PE, Molecular Probes, Eugene, Oreg.) was used as the secondary reagent to report 7E11.C5 or 399. CAM 5.2, a fluorescein conjugated antibody directed against cytokeratin 8 and 18, was purchased directly from the manufacturer (Becton Dickinson, San Jose, Calif.). DNA was stained using To-Pro 3 (Molecular Probes, Eugene, Oreg.). Excitation of this dye is accomplished with the 635 nm laser and can be detected in a 661 +/−8 nm bandpass detector without further compensation in the FITC and PE detectors. To-Pro 3 has been used in three-color flow cytometry in the testing of skin melanoma. Doornbos et al., 1994, Cytometry 15:267–271; Glade et al., 1996, Arch. Dematol. Res. 288:203–210; van Hooijdonk et al., 1994, Cytometry 17:185–189. By using the antibodies to PSMA and cytokeratin, as well as the DNA stain To-Pro 3, viable prostate cells in semen, in normal as well as prostate cancer patients, are identifiable.

$3 \times 10^6$ round cells per clinical sample were stained per flow cytometry run. $2 \times 10^4$ control cells of PNCF 007 or PC-3 and LNCAP were run as well. Cells were stained with either 7E11.C5 (anti-PSMA) or 399 (anti-PSA). The 7E11.C5 or 399 were added to samples at concentrations of 20 $\mu$g per ml/$10^6$ total cells. CAM 5.2 was used at a concentration of 8 $\mu$g per total cells in 1% Bovine Serum Albumin (BSA), in PBS (BSA, Sigma Chemical Company, St. Louis Mo.). The patient samples and the control samples were incubated 1 hour on ice. The cells were washed with 2 ml of 1% BSA in PBS and pelleted by centrifugation at 400×G for five minutes. Streptavidin conjugated phycoerythrin (PE) (Molecular Probes, Eugene, Oreg.) was added to each sample at a concentration of 1 $\mu$g per ml/$10^6$ total cells in 1% BSA in PBS. The cells were incubated thirty minutes on ice, and again were washed with 2 ml of 1% BSA in PBS and pelleted by centrifugation at 400×G. The cells were re-suspended in 1% BSA in PBS with 1 $\mu$g of To-Pro 3 plus 1.5 Koontz units RNAse (Sigma Chemical Company, St. Louis Mo.) per 0.5 ml/$10^6$ total cells. The samples were allowed to incubate for 30 minutes at room temperature. The samples were filtered through a 35 μm mesh prior to analysis, within two hours after the addition of the To-Pro 3.

Semen was assayed using a Becton Dickinson FACSCaliber Cytometer with the basic four-color option, (Becton Dickinson, San Jose, Calif.). The machine was equipped with two lasers, a helium neon laser tuned to 488 nm and a diode laser tuned to 635 nm. The filter sets were the basic four color option FL-1 530 +/−15 nm, FL-2 585 +/−21 nm, FL-4 661 +/−8 nm and FL2>670 nm. Time delay calibrations, to account for the separations of the two lasers, were done using APC conjugated beads (Becton Dickinson, San Jose, Calif.), according to manufacture's specifications prior to each session. Forward, side scatter, and the fluorescent intensities were collected simultaneously at a rate of up to 1500 events per second. Overlap of the various fluorochromes was compensated for electronically during the run. For most runs the compensation setting would be: FL1−%FL2=2.0 and FL2−%FL1=34.0. Typically it was not necessary to compensate for the To-Pro 3 signal. Data was stored and analyzed on a Macintosh 7600 computer using Cell Quest software from Becton Dickinson.

Control samples were used to adjust the detectors and compensation of the fluorochrome. The negative control cells, PC-3 or PNCF 007, were used to set the voltage to the photomultiplier tube of the FL-1 detector and FL2 detector as well as forward (cell size) and side scatter (internal complexity). Voltages were adjusted so that the mean of the histogram of the negative cell line was 4 for FL-1 height and FL-2 height. Cells that were stained only by To-Pro 3 were used to adjust the FL-4 signal width and signal area for purposes of doublet discrimination. The 7E11.C5 and CAM 5.2 positive cell line LNCAP was used for the purpose of adjusting compensation. Each run included a reference sample with a known ratio of LNCAP, PC-3 and PNCF 007. The flow cytometer's flow cell and lines were washed out with 10% bleach and water between the running of semen sample and the controls to eliminate any possible carryover. Voltage adjustments were made to the DNA detector to account for differences in the DNA staining of the control cells and the samples.

Data were collected for each control and each sample until the total number of cycling cells exceeded 10,000 events. However, in cases of large cell numbers in excess of 50,000 cycling events were collected. A minimum level of 10,000 cycling events was sufficient to yield 1,0002,000 round cells. Gating decisions were made on the basis of positive and negative stained cells. A positive gate must exclude 99% negative stained PC-3 or PNCF-007 cells and include 85% of PSMA-positive stained LNCAP cells. The bias in this gating scheme was such that only robustly stained cells were included in the analysis.

6.2 RESULTS

The final results of samples were based on a progressive gating scheme that utilized DNA staining, and forward and side scatter characteristics. The first gate was applied to the DNA signal width versus signal area graph to identify the cycling, diploid population. The forward scatter versus side scatter graph was used to exclude non-sperm cells. Events that satisfied the combined gates were then represented on a two-dimensional log fluorescence graph. The cytokeratin fluorescence staining is represented horizontally, and PSMA or PSA staining is represented vertically. Utilizing this specific protocol, sperm cells were eliminated from the analysis.

Figure 1A:
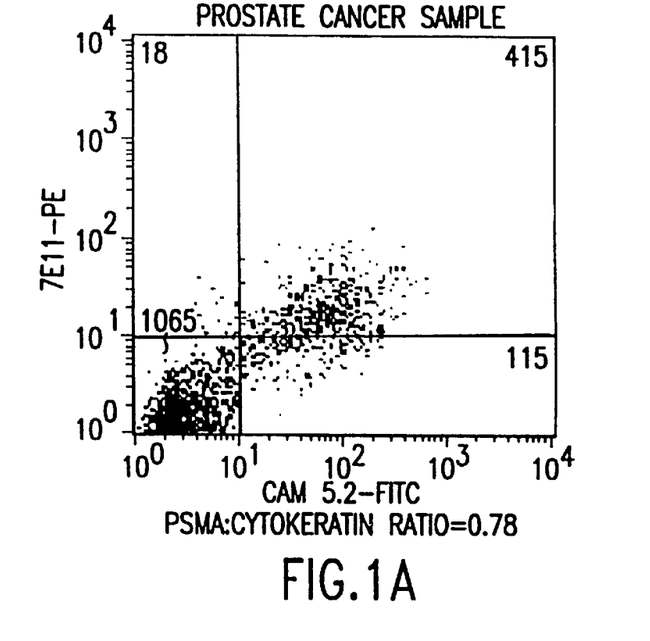
FIGS. 1A and 1B are representative dot plots of cells binding antibody to PSMA and to cytokeratin from a prostate cancer patient (FIG. 1A) and a patient without any evidence of disease (FIG. 1B). These graphs were generated from the cycling populations as determined by DNA pulse width and area graphs. Quadrants are based on the staining of the control cells LNCAP (CAM 5.2 +, 7E11.C5+) and PC-3 (isotype control-FITC, 7E11.C5−) that were run in conjunction with the samples. The prostate cancer patient sample demonstrates the 7E11.C5 positive staining of the cytokeratin population and the relative lack of staining of the cytokeratin population in the normal group.
Figure 1B:
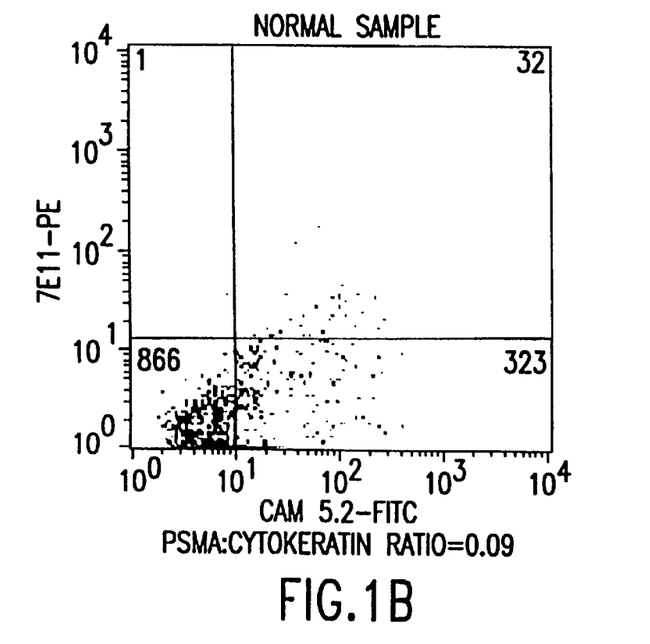

FIG. 1A is a representative dot plot of cells stained with 7E11.C5 and CAM 5.2, which were obtained from the semen of a vasectomized prostate cancer patient with localized disease, and FIG. 1B is a representative dot plot of stained cells which were obtained from a semen sample from an individual without prostate disease (7E11.C5 staining vertically and CAM 5.2 staining horizontally). The lower left quadrant demonstrates the bulk of cells that do not stain for either marker. In the right hand region, the CAM 5.2 positive cells were evident in both the cancer patient and the normal individual. The upper right quadrant of FIG. 1A (the prostate cancer patient graph) shows the 7E11.C5 positive and cytokeratin positive cells. The individual with no evidence of disease (FIG. 1B) had positive CAM 5.2 staining, however the cell population was predominately negative for 7E11.C5. The vast majority of cells in both the cancer patient and the individual with no evidence of disease stained negative for cytokeratin and PSMA. The negative cytokeratin staining population is comprised of leukocytes, urothelial and seminal vesicle cells. Gardiner et al., 1996, Br. J. Urol. 78:414–418; B'Elanger et al., 1994, Prostate 27:187–197.

Figure 2A:
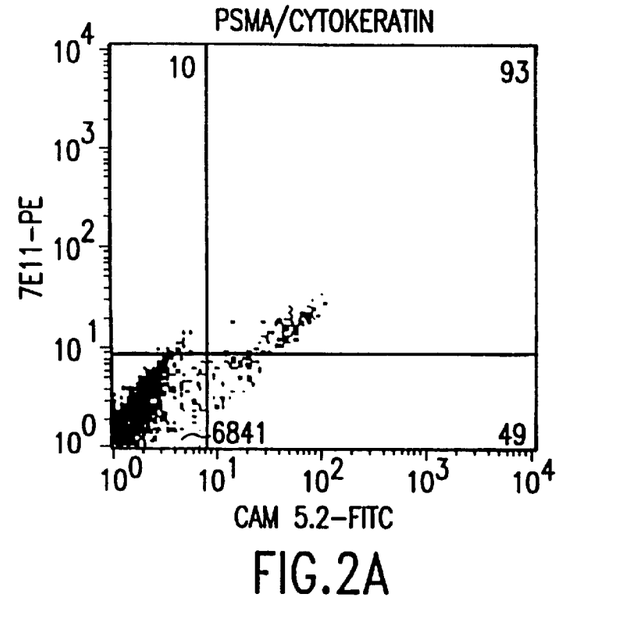
FIGS. 2A and 2B are representative dot plots of cells from a prostate cancer patient showing the comparative PSMA and PSA staining. These graphs were generated from the cycling populations as determined by DNA pulse width and area graphs. Quadrants are based on the staining of the control cells LNCaP (CAM 5.2 7E11.C5 +, PSA +) and PNCF 007 (CAM 5.2 −, 7E11.C5−, PSA −) that were run in conjunction with the samples. PSMA/cytokeratin staining is demonstrated in FIG. 2A (CAM 5.2 positive cells only stained positive for PSMA) and PSA/cytokeratin staining in FIG. 2B (CAM positive and CAM negative cells stained with PSA).
Figure 2B:
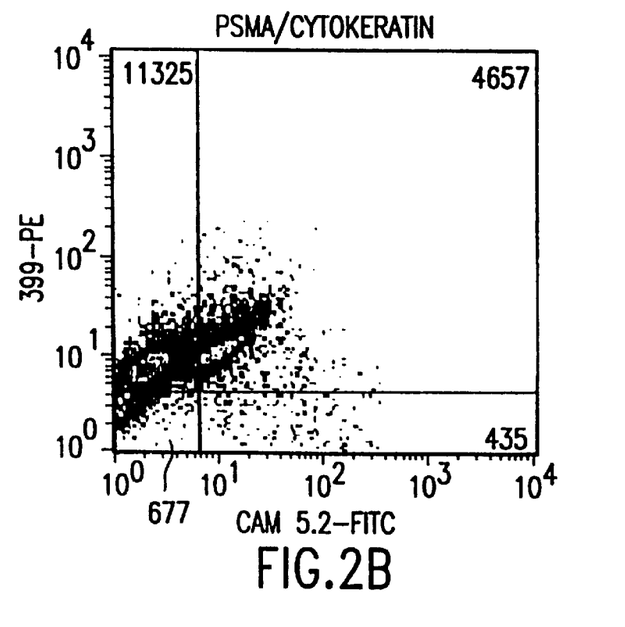

A split sample from a prostate cancer patient was stained with either 7E11.C5/CAM 5.2 or with anti-PSA antibody 399/CAM 5.2. The results are shown in FIGS. 2A–2B. These figures demonstrate the similar pattern of staining for cancer patients, in that a significant percentage of the CAM 5.2 positive population stains with 7E11.C5 (FIG. 2A). PSA staining is demonstrated in FIG. 2B. It is evident that the antibody to PSA is staining non-epithelial cells in addition to the cytokeratin positive population. Several other samples were split and stained in this manner. Although the PSMA and cytokeratin staining were constant, the PSA staining was, at best, variable.

The mean number of cycling cells collected per cancer sample and normal sample was 17,370 and 11,497 respectively. The mean number of CAM 5.2 positive cells per run was 1,742 for prostate cancer patients and 3,326 for patients without evidence of prostate cancer. From the total population of CAM 5.2 positive cycling cells, the mean number of 7E11.C5 staining cells was 1,060 for prostate cancer patients and 324 for patients without evidence of prostate cancer. Total cell numbers varied according to the total cell population, the amount of debris in the sample, and the presence of sperm. The range of total cycling cells varied from a minimum of 716 to a maximum of 109,987. During acquisition, the targeted number of cycling events was 10,000. If sufficient cells were available, the collection continued beyond 10,000.

Figure 3:
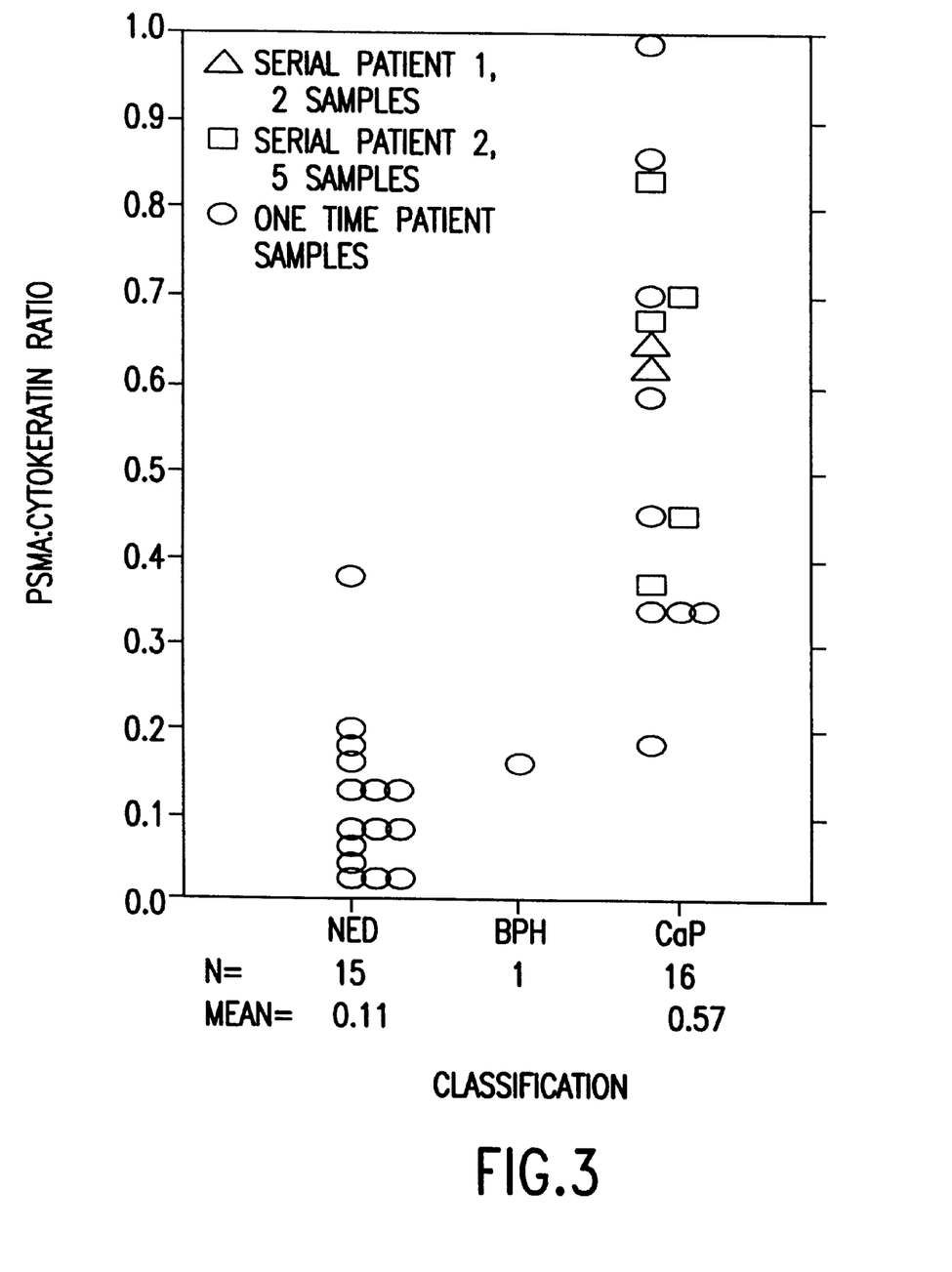
FIG. 3 is a graph showing the distribution of the ratio of PSMA-positive cells:cytokeratin-positive cells in subjects free of prostate cancer (NED), a subject having benign prostatic hyperplasia (BPH) and subjects having prostate cancer (CaP). Subjects who had more than one sample tested are indicated by a triangle (2 samples) or a square (5 samples). Subjects who had a single sample tested are indicated by a circle.

Because of the large variation in total numbers of cells from sample to sample, the 7E11.C5 results were normalized to the total epithelial cell population by dividing the 7E11.C5 positive cells by the total number of CAM 5.2 positive cells. This ratio is called the PSMA:cytokeratin Ratio. The PSMA-cytokeratin ratios observed in 31 samples are shown in FIG. 3. FIG. 3 demonstrates the elevation of the total 7E11.C5 positive population in prostate cancer patients versus patients with no evidence of prostate cancer. The clinical stage of the cancer patients is shown in Table II. The mean PSMA:cytokeratin ratio from 16 samples from prostate cancer patients was 0.57 and for the 15 samples from individuals with no evidence of disease the ratio was 0.11. A BPH sample (biopsy proven) is also represented in FIG. 3. The difference in ratio between the normal and cancer groups was significant, as the MANOVA probability was <0.005 using 3 degrees of freedom and the correlation (r) equals 0.725.

Figure 4A:
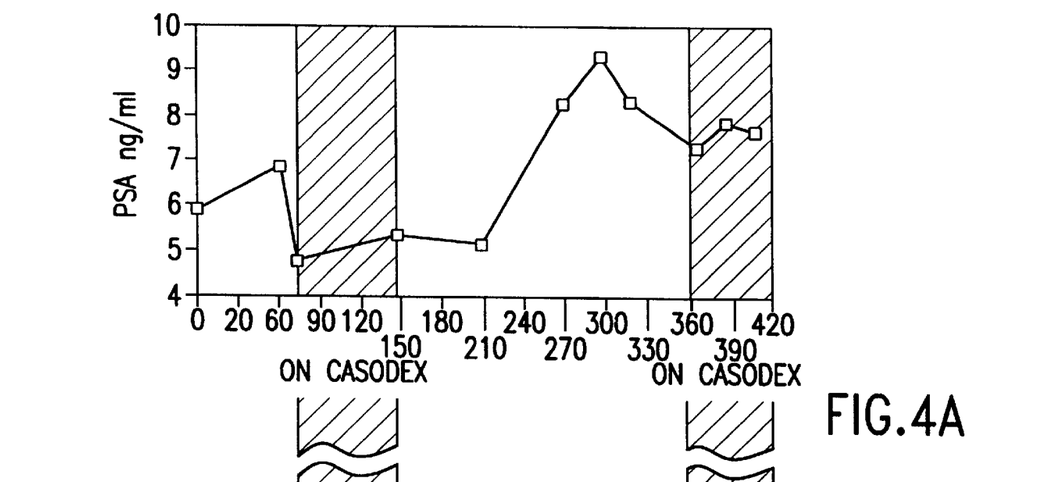
FIGS. 4A and 4B are graphical depictions of PSA levels (FIG. 4A) and PSMA:cytokeratin ratios (FIG. 4B) observed in a prostate cancer patient undergoing anti-androgen treatment. The time during which the patient was treated with the anti-androgen is depicted by the shaded areas labeled "On Casodex". Biopsies were taken at day 70 and 345 and the biopsy results are shown in the boxes and demonstrate the growth of the tumor over a one year period as reflected in the PSA levels and the changing PSMA:cytokeratin ratio.
Figure 4B:
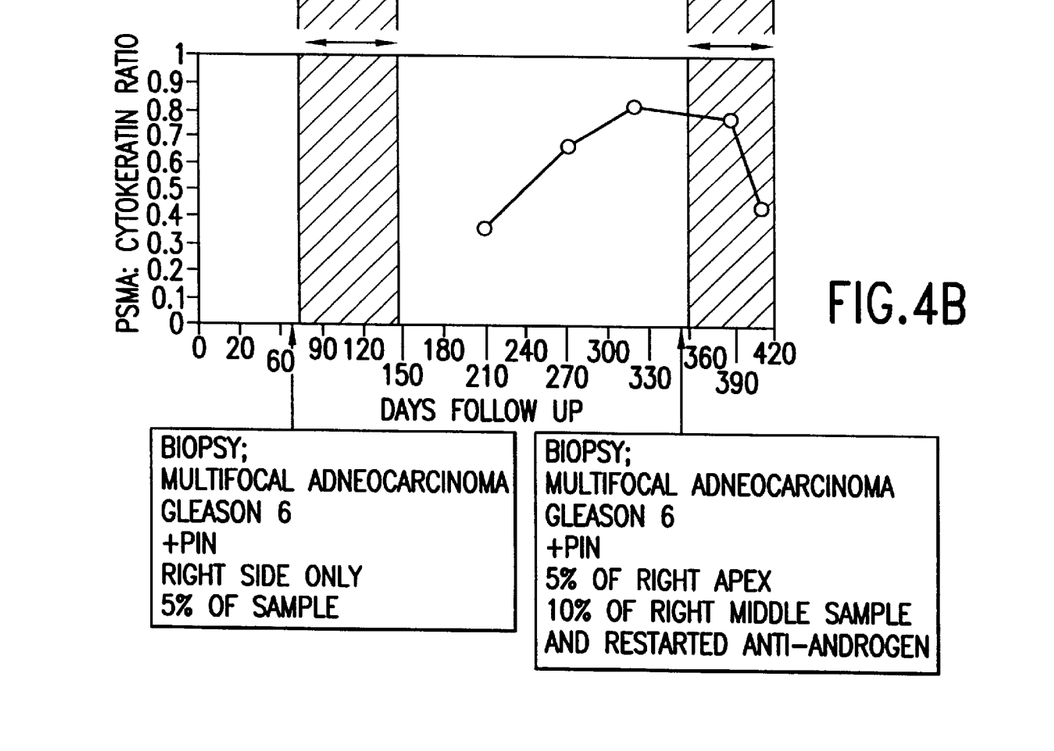

A vasectomized prostate cancer patient (stage T1a) was followed after primary hormone ablation therapy. Semen samples were not collected during the medication period due to the anti-androgen effects which resulted in little semen. A biopsy prior to the therapy identified prostate tumor in 5% of the right apex sample. A biopsy 200 days after the medication was stopped identified prostate tumor in 10% of the right apex and 5% of the right mid sample. FIGS. 4A and 4B demonstrate serial PSMA:cytokeratin Ratios as the disease progressed in this patient.

6.3 DISCUSSION

The observation that the basal and stromal cell layer are degraded as tumors advance, suggests that prostate cell numbers in the semen of prostate cancer patients should increase and that an elevated expression of PSMA should be seen in prostate cancer cells compared to cells present in the semen from individuals free of prostate cancer. See, Bostwick et al., 1996, Prostate 29:117–134; Kleinerman et al., 1995, Cancer Res. 55:1215–1220. The results presented above are consistent with this hypothesis, in that there are greater numbers of prostate cells in the semen of prostate cancer patients as compared to patients free of prostate cancer. However, the simple raw cell counts of 7E11.C5 positive and CAM 5.2 positive cells do not provide for any clinical measure due to the generally low CAM 5.2 positive cell frequency and wide variability of numbers of cells in any given sample. By normalizing the number of 7E11.C5 positive cells to the total number of epithelial cells via the prostate cell:epithelial cell ratio, comparisons can be made between cancer patients and normal individuals and such comparisons can be advantageously useful to detect prostate cancer.

Figure 5:
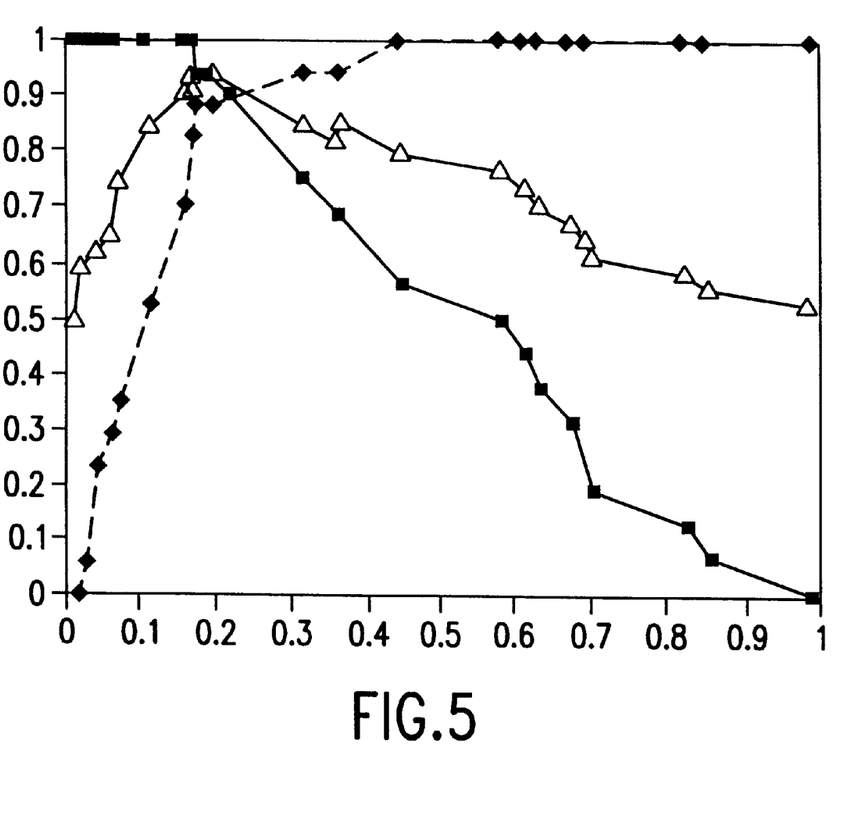
FIG. 5 is a Receiver-operator characteristic plot which demonstrates that in this illustrative example the cut value above which an individual is classified as having cancer was determined to be 0.21 by maximizing the sensitivity (positive-predictive ability) and specificity (negative-predicitve ability) of the assay. The intersection of the specificity curve and the sensitivity curve is the point of maximum sensitivity and specificity. See Section 6 for details. Specificity curve, --●--; sensitivity curve, --■--; accuracy curve, --Δ--.

Results presented in FIGS. 1A and 1B demonstrate the presence of PSMA positive cells in the cancer patient and to a much lesser degree in the patient without prostate cancer. FIG. 3 shows that by using a ratio of PSMA:cytokeratin positive cells, distinguishing prostate cancer patients from those without disease is possible. In individuals free of prostate cancer, the ratio was calculated to be about 0.024 to about 0.38, with a mean of 0.11; in individuals with prostate cancer, the ratio was calculated to be about 0.121 to about 0.994, with a mean of 0.57. This difference is significant with a p value <0.005. These results were subjected to analysis using a receiver-operator characteristic plot (ROC), shown in FIG. 5, which indicated that, in this illustrative example, the "cut value" at which an individual was classified as positive was 0.21. This value is the point at which the sensitivity curve and specificity curve intersect. The sensitivity curve is obtained by graphing (number of true-positive test results)/(number of true-positive test results + number of false-negative test results). The specificity curve is obtained by graphing (the number of false-positive test results)/(number of true negative test results + number of false-positive test results).

The results above show that the detection of prostate cells in semen alone does not provide useful clinical information. Prognostic markers such as PSMA need to be included in the over all evaluation panel. An up-regulation in PSMA expression in prostate tumors has been observed. The overexpression of PSMA, observed in higher Gleason grade tumors, generates a higher PSMA:cytokeratin ratio in semen samples, as demonstrated herein. The ability to measure the expression of PSMA with the flow cytometer with greater accuracy than by more subjective means, such as microscopic, permits a more clinically relevant analysis.

The advantage of a noninvasive cytological based test for prostate cancer is that patients can be followed more frequently without repeated biopsies. To demonstrate the value of this approach the clinical progress of a T1a prostate cancer patient during the course of hormone treatment was followed. FIGS. 4A and 4B show the serial PSA values as well as the ratios of prostate cells:epithelial cells at roughly 2-month intervals. Prior to hormone therapy with Casodex, this individual underwent a sextant core biopsy. The results of the initial biopsy showed 5% of the sample from the right side core was adenocarcinoma with a Gleason score of 6. The sample included prostatic intracellular neoplasia (PIN), which is a prostate cancer precursor lesion. Two hundred days after the completion of hormone therapy, the patient underwent another sextant biopsy after two successive rises in his PSA level. This biopsy showed an increase in the size of the tumor to 10% of the right middle sample and 5% of the right apex compared to the original 5% of the biopsy sample. Concurrently, over this time period the prostate cells:epithelial cell ratio and the concurrent rise in PSA mirrored the growth of the tumor.

PSA staining was unable to provide any additional clinical information. FIGS. 2A and 2B demonstrate the PSA-cytokeratin, and the PSMA-cytokeratin staining on a split sample from a prostate cancer patent. There was positive cytokeratin staining in both samples. However, the PSA stained the negative cytokeratin population as well as the positive cytokeratin cell population. 7E11.C5 stained only the cytokeratin positive population and not the negative population. PSA is expressed in the mature secretory glandular cells of the prostate. Sinha et al, 1987, Cancer Res. 60:1288–1293. These cells are identified by the expression of cytokeratin 8 and 18. Moll et al., 1982, Cell 31:11–24; Leader et al., 1986, Histopathology 10:1315–1324; Verhagen et al., 1992, Cancer Res. 52:6182–6187. The positive staining of the negative cytokeratin population was unexpected. This positive PSA staining of cytokeratin negative cells may be the result of the large concentrations of PSA in the ejaculate and the subsequent large background of PSA still "adsorbed" to irrelevant cells.

Figure 6A:
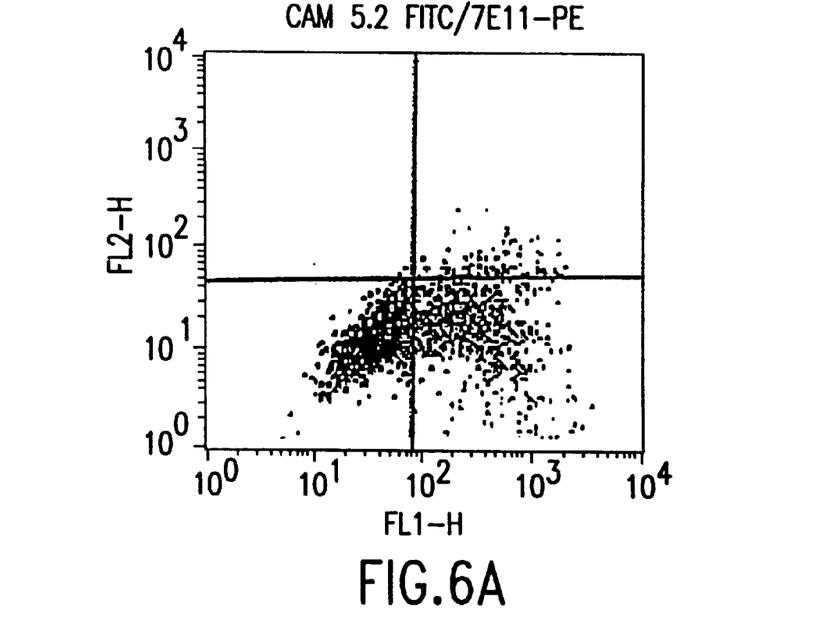
FIGS. 6A and 6B are representative dot plots of cells from a split semen sample binding antibody to PSMA and to cytokeratin with different fluorescent dyes.
Figure 6B:
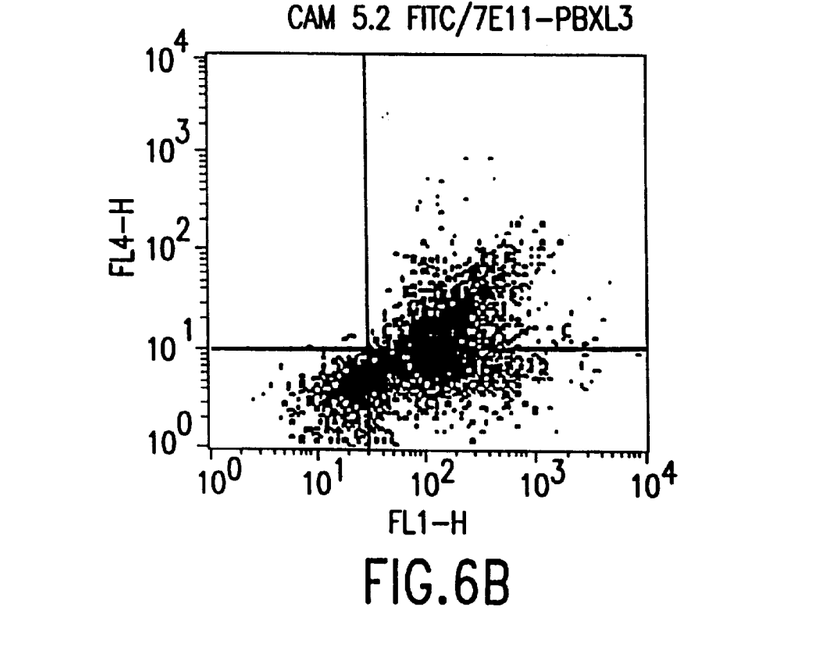

A similar experiment for detection of PSMA-positive and epithelial cells was performed as described above but used different fluorescent dyes to insure that the staining of the PSMA-positive prostate cells was not dye specific. FIGS. 6A and 6B are representative dot plots in which the PSMA cells were detected using the dye r-phycoerythrin (PE) (FIG. 6A) or the dye Phycobilisome-3 (FIG. 6B). By comparing FIGS. 6A and 6B, it is clearly shown that the staining of the prostate cells was not dye specific.

The invention claimed and described herein is not to be limited in scope by the specific embodiments herein disclosed since these embodiments are intended as illustrations of several aspects of the invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which are incorporated herein, in their entirety, by reference.

What is claimed is:

1. A method for the detection of prostate cancer comprising, determining the ratio of the number of prostate cells and the total number of epithelial cells in a body fluid sample, in which the ratio is elevated in individuals with prostate cancer as compared to individuals free of prostate cancer.

2. The method according to claim 1 in which the ratio is determined by (1) quantifying the number of prostate cells in a bodily fluid sample; (2) quantifying the total number of epithelial cells in the sample; and (3) calculating the ratio of the number of prostate cells to the total number of epithelial cells.

3. The method according to claim 2 in which the quantifying steps (1) and (2) are performed simultaneously.

4. The method according to claim 3 in which a flow cytometer is employed.

5. The method according to claim 2 in which the number of prostate cells is quantified by using an antibody or portion thereof that binds to a prostate cell-specific marker.

6. The method according to claim 5 in which the prostate cell specific marker is selected from the group consisting of prostate-specific antigen (PSA), prostate-specific membrane antigen (PSMA), prostate secretory protein (PSP), prostate acid phosphatase (PAP), human glandular kallekrein 2 (HK-2), prostate stem cell antigen (PSCA) and PTI-1.

7. The method according to claim 5 in which the number of prostate cells is quantified by using an antibody that binds to PSMA.

8. The method according to claim 7 in which the antibody is 7E11.C5 (produced by the hybridoma deposited at the ATCC and assigned Accession No. HB-10494).

9. The method according to claim 7 in which the antibody is directly labeled with a fluorescent marker.

10. The method according to claim 7 in which the antibody is indirectly labeled with a fluorescent marker.

11. The method according to claim 2 in which the total number of epithelial cells is quantified by using an antibody that binds to an epithelial cell-specific marker.

12. The method according to claim 11 in which the epithelial cell-specific marker is cytokeratin or epithelial cell adhesion molecule (EPCAM).

13. The method according to claim 12 in which the marker is cytokeratin and the antibody is selected from the group consisting of CAM 5.2, 5D3, LP34, UCD/Ab6.11 (produced by the hybridoma deposited at the ATCC and assigned Accession No. HB8458), UCD/Ab6.01 (produced by the hybridoma deposited at the ATCC and assigned Accession No. HB-8693) and UCD/PR0.11 (produced by the hybridoma deposited at the ATCC and assigned Accession No. HB-8694).

14. The method according to claim 11 in which the antibody is directly labeled with a fluorescent marker.

15. The method according to claim 11 in which the antibody is indirectly labeled with a fluorescent marker.

16. The method according to claim 1 in which the body fluid is semen and the total number of epithelial cells is quantified using an antibody that binds to an epithelial cell-specific marker.

17. The method according to claim 1 in which the body fluid is blood.

18. The method according to claim 1 in which the body fluid is urine.

* * * * *